United States Patent
Belenger et al.

(10) Patent No.: US 7,721,843 B1
(45) Date of Patent: May 25, 2010

(54) VISUAL ACOUSTIC DEVICE

(75) Inventors: Robert V. Belenger, Raynham, MA (US); Gennaro Lopriore, Somerset, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1143 days.

(21) Appl. No.: 11/357,470

(22) Filed: Feb. 8, 2006

(51) Int. Cl.
- A61B 7/02 (2006.01)
- A61B 5/02 (2006.01)
- A61B 5/024 (2006.01)
- A61B 7/04 (2006.01)

(52) U.S. Cl. .......... 181/131; 381/67; 600/528; 600/523

(58) Field of Classification Search ........ 181/131; 381/67; 600/528, 527, 523, 509, 508
See application file for complete search history.

(56) References Cited

U.S. PATENT DOCUMENTS

| | | | |
|---|---|---|---|
| 2,772,672 A * | 12/1956 | Losner | 600/508 |
| 3,321,905 A * | 5/1967 | Krebs | 368/232 |
| 3,858,005 A * | 12/1974 | Marshall et al. | 600/528 |
| 4,653,930 A * | 3/1987 | Schmid | 368/77 |
| 4,672,975 A | 6/1987 | Sirota | |
| 4,761,253 A * | 8/1988 | Antes | 264/1.31 |
| 4,783,813 A | 11/1988 | Kempka | |
| 4,972,841 A * | 11/1990 | Iguchi | 600/528 |
| 5,010,889 A * | 4/1991 | Bredesen et al. | 600/528 |
| 5,309,767 A * | 5/1994 | Parmar et al. | 73/705 |
| 5,638,453 A | 6/1997 | McLaughlin | |
| 5,737,429 A | 4/1998 | Lee | |
| 5,983,727 A * | 11/1999 | Wellman et al. | 73/724 |
| 6,249,588 B1 * | 6/2001 | Amidror et al. | 382/100 |
| 6,396,931 B1 | 5/2002 | Malilay | |
| 6,494,491 B1 * | 12/2002 | Zeiter et al. | 283/91 |
| 6,661,897 B2 * | 12/2003 | Smith | 381/67 |
| 7,043,292 B2 * | 5/2006 | Tarjan et al. | 600/509 |
| 7,295,717 B2 * | 11/2007 | Hersch et al. | 382/276 |
| 7,300,406 B2 * | 11/2007 | Carter | 600/528 |
| 7,527,123 B2 * | 5/2009 | Puder | 181/131 |
| 2001/0030077 A1 | 10/2001 | Watson | |
| 2002/0071570 A1 | 6/2002 | Cohen et al. | |

FOREIGN PATENT DOCUMENTS

JP 03048294 A * 3/1991

OTHER PUBLICATIONS

Moire Pattern- Encyclopedia Brittanica Online; http://www.brittanica.com. Retrieved on Dec. 9, 2009.*

* cited by examiner

Primary Examiner—Edgardo San Martin
(74) Attorney, Agent, or Firm—James M. Kasischke; Jean-Paul A. Nasser; Michael P. Stanley (57) ABSTRACT

A visual-acoustic device is provided that contains an acoustic detector to produce sound waves in communication with a moiré pattern generator that produces moiré patterns corresponding to the sound waves. The device includes a rigid plate having a first repetitive pattern and a flexible plate spaced from the rigid, plate and having a second repetitive pattern corresponding to the first repetitive pattern. The sound waves induce movement of the flexible plate such that the second repetitive pattern moves with respect to the first repetitive pattern to produce the moiré pattern. The visual-acoustic device can be arranged as a visual-acoustic stethoscope.

20 Claims, 6 Drawing Sheets

VISUAL ACOUSTIC DEVICE

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention is directed to acoustic devices. In particular, the present invention is directed to diagnostic medical equipment such as stethoscopes.

(2) Description of the Prior Art

Auscultation is the act of listening to the sounds from internal organs of the body. These sounds are used to diagnose abnormalities or disorders in the internal organs for the purpose of prescribing appropriate treatments. The instrument commonly used for auscultation is the acoustic stethoscope, which is one of the most utilized instruments of health care providers. In order to use the stethoscope, an acoustic bell is placed on the body over the organ of interest. The sounds received by the bell are conveyed through a tubular line to ear pieces that are inserted into a physician's ears. Because a stethoscope is a non-invasive means for auscultation, it is an invaluable tool for the medical diagnosis of abnormalities, particularly cardiac, lung and vascular disorders.

The effectiveness of a stethoscope depends on both the ability to conduct body sounds to the ear and the skill and hearing ability of the user. A conventional acoustic stethoscope acts as a low-pass filter. Therefore, the higher frequencies associated with the internal body sounds are filtered out. In addition, a user with poor hearing is less likely to be able to interpret the body sounds delivered through the tubular line. The frequency range for audible sounds is from about 10 Hz to about 15500 Hz; however, most people are not able to hear sounds across the entire audio frequency range. Age and ear disorders cause a decrease in the sensitivity of the ear, in particular to higher frequencies. These limitations can cause a physician to have a distorted or inadequate impression of the sounds originating from the internal organ, which could lead to a misinterpretation of the medical significance of these sounds.

Attempts at overcoming the limitations of conventional acoustic stethoscopes involve amplifying the sounds obtained by the acoustic bell and providing visual indicators of the sounds or functions of internal organs. For example, U.S. Pat. No. 4,672,975 is directed to a stethoscope that includes an electronic device that produces an image of an expanding and contracting heart. The image of the expanding and contracting heart either does not represent actual heart activity of a patient and instead only serves the purpose of entertaining the patient or is formed in correspondence with the heart beats of a patient. The contracting and expanding heart is represented by light emitting diodes or a liquid crystal display, and the image is not limited to a heart-shaped image. The disclosed stethoscope, however, requires a multitude of electronic components including batteries, microphones and other circuitry. All of these components add size, weight, cost and complexity to the stethoscope. Also, the visual image is directed specifically and solely to an indication of patient heart rate.

U.S. Pat. No. 4,783,813 is directed to an electronic sound amplifying stethoscope with visual heart beat and blood flow indicator. The amplification circuitry includes a battery, a microphone and a speaker. A light emitting diode (LED) light source is inserted in series with the amplifier circuit, a switch and the battery. The current flow to the amplifier circuit also energizes the LED such that the intensity of the LED is directly proportional to the volume of sound amplified. The current flow through the LED is responsive to the current fluctuations or power surges in the amplifier and speaker. This stethoscope contains electronic circuitry that requires a power source and adds to the complexity, weight and cost of the stethoscope. Also, although the intensity of the LED changes, it is not clear how this intensity indicates a particular type of body function or any particular qualities of a body function. The LED intensity only indicates the intensity of the audio signal that is being amplified.

U.S. Pat. No. 5,638,453 is directed to a transducer enhanced stethoscope that measures skin temperature and heart rate in addition to amplifying the sound that is transmitted through the stethoscope. The stethoscope includes a pickup head having a top face that includes a pair of semi-circular temperature sensors capable of measuring skin temperature and displaying it on a top readout screen. The bottom face of the pickup head has a semi-circular pulse sensor that uses a transducer to determine the pulse of the body, displaying this information on a bottom readout screen. A battery is housed within the pickup head. This stethoscope requires rather complex electronics and a power source such as a battery that add to the size and cost of the stethoscope. In addition, the electronics are selected to measure and display two specific body measurements, temperature and pulse rate. No visual indication of the heart rate or any other body sound is provided.

U.S. Pat. No. 5,737,429 is directed to a portable, viewable and audible stethoscope for visually and audibly monitoring vital life signs such as heart beat, lung respiration, artery pulse and intestinal sounds. The stethoscope includes sound absorbing cups in contact with an output device that includes a microphone that converts the sounds coming from the absorbing cups into electrical signals. The output device includes an oscilloscope and an electronic circuit assembly for displaying the electrical signals as graphs on the oscilloscope. In order to create a visual indication of the monitored functions, a completely separate assembly that includes an oscilloscope with a picture screen and the necessary control circuitry is used. The oscilloscope is likely to have a significant power demand and associated cost. Therefore, this solution is complex and has a high associated cost.

U.S. Pat. No. 6,396,931 is directed to an electronic stethoscope with diagnostic capability that provides means for comparing a stethoscope sound and oscilloscope image with a typical sound and identified image that has been prerecorded on a magnetic memory disc. Various heart and lung sounds are prerecorded along with a very short diagnosis of the defect causing the sound. If a technician suspects any disorders, that technician presses an appropriate button and adjusts a sliding switch to the location at which matching sounds are heard and seen from a prerecorded diskette. This system is not simply amplifying the sounds of a stethoscope or providing a visual analogue of the sounds. The system is a complex diagnostic tool that requires prerecorded comparisons that a skilled technician can use to determine if the sounds that are heard correlate to a specific condition.

U.S. Patent Application Publication No. US2001/0030077 is directed to a stethoscope with ECG monitor for monitoring and displaying heart sounds and heart electrical activity. The system uses an electronic stethoscope head combined with a standard stethoscope air tube headset assembly. The stethoscope head includes an electrode assembly that conducts electrical signals to a display module that is mounted on the stethoscope body. The display module includes a housing containing an electrical signal processor, a battery power supply and a view screen. The view screen presentation includes a waveform presentation of the heart electrical signal. Other sensor and diagnostic features can also be included such as a blood hemoglobin oxygen saturation sensor and blood sugar detectors. Again, this device requires various electronic components and a power supply, adding complexity and cost to the stethoscope. In addition, the visual information presented is not simply a visual indication of the audible information detected by the stethoscope but is additional diagnostic information that is provided by separate sensors that are specifically arranged and selected to provide a particular type of information.

U.S. Patent Application Publication No. US2002/0071570 is directed to a hybrid stethoscope that enables a physician to hear sounds emanating from an internal region and to concurrently see an analogue waveform of these sounds. The hybrid stethoscope includes a self-sufficient battery-powered visual display module attached to the rear end of the acoustic bell. The display module is provided with a liquid crystal display (LCD) or similar device to exhibit an analog waveform of the audible sounds impinging on the diaphragm of the bell and conveyed to the ears of the physician. This is an electronic system that requires power, a microphone, a liquid crystal display, integrated circuits and other electronic components. The output is a waveform that needs to be related to the body system being monitored and the sounds impinging on the bell.

Therefore, the need exists for a stethoscope that is capable of monitoring sounds produced by internal organs and of simultaneously delivering an audible output of these sounds and a corresponding visual indication. The combined audible and visual output can be used for any type of internal organ and does not require complex or expensive electrical components that have a significant power demand.

SUMMARY OF THE INVENTION

Exemplary embodiments of stethoscopes in accordance with the present invention utilize moiré patterns to provide a visual analogue of the sounds obtained by the stethoscope. Moiré patterns appear when two repetitive patterns of lines, circles, grids, dot arrays and other patterns are overlapped at an angle or with imperfect alignment, magnifying differences between the two repetitive patterns. If two identical patterns are exactly aligned no moiré pattern appears. If two or more dissimilar patterns are overlapped, they may establish base patterns by their interference, and they can also create moirés. The slightest misalignment of two or more patterns can create large scale, easily visible moiré patterns. As the misalignment increases, the lines of the moiré pattern will diverge or converge in ways that can be interpreted relative to the sound or pressure change creating the misalignment.

Visual-acoustic stethoscopes in accordance with exemplary embodiments of the present invention exploit this phenomenon to provide a visual means of presenting different body sounds by using these sounds to distort, and therefore misalign, two overlapping repetitive patterns, producing moiré patterns. Variations in sound qualities such as pitch, tone, volume, amplitude, frequency and pattern result in variations in the misalignment of two patterns, producing variations in moiré patterns. The various moiré patterns are associated with pre-determined sounds for both normal and abnormal internal organ function. Therefore, by viewing a given moiré pattern associated with the stethoscope, a visual indication of an evaluation of a person's health is provided.

DETAILED DESCRIPTION

Figure 1:
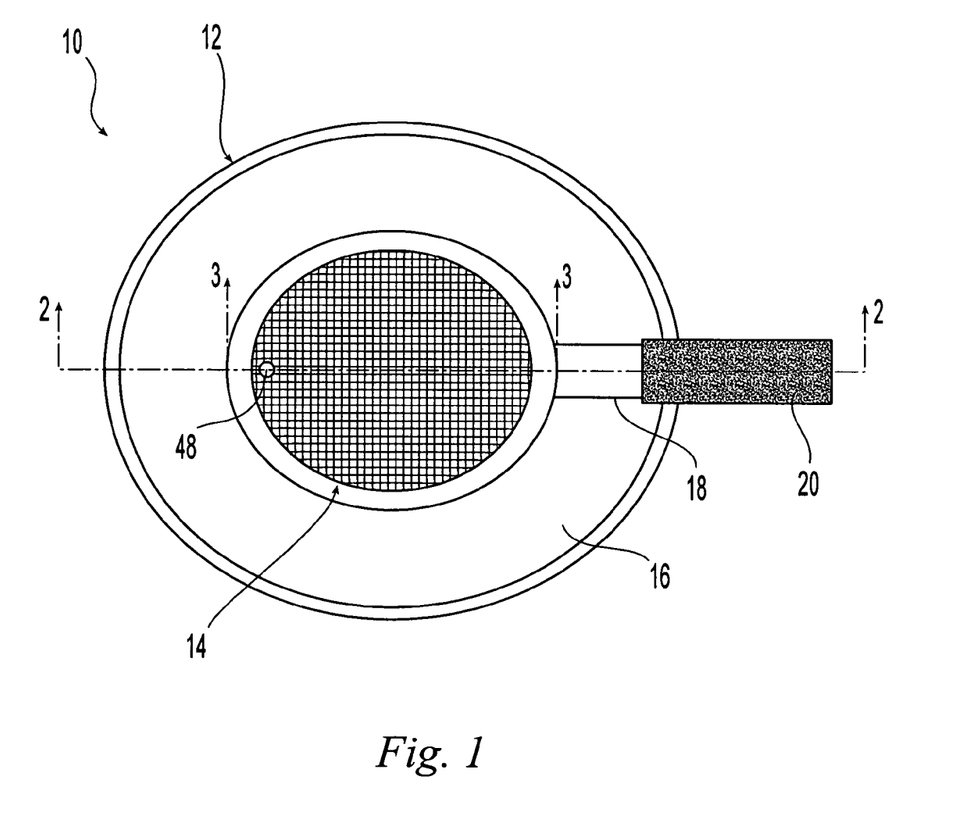
FIG. 1 is top view of an embodiment of a visual acoustic stethoscope in accordance with the present invention.
Figure 2:
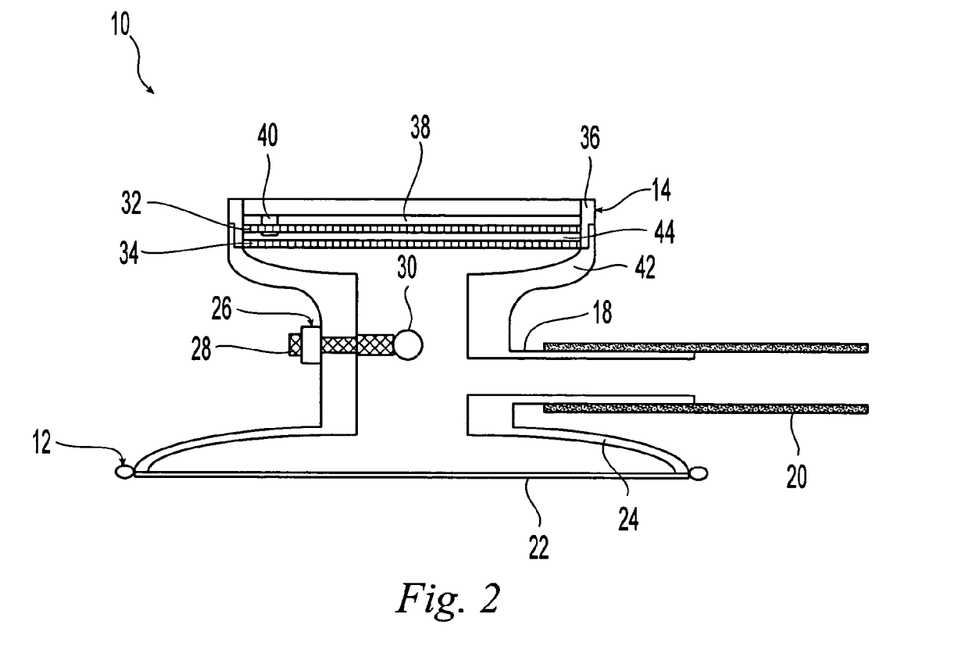
FIG. 2 is a view through line 2-2 of FIG. 1.

Referring initially to FIGS. 1 and 2, a visual-acoustic device 10 in accordance with an exemplary embodiment of the present invention is illustrated. As illustrated, the visual-acoustic device is a visual-acoustic stethoscope. The visual-acoustic stethoscope is used for illustrative purposes, and visual-acoustic devices in accordance with the present invention are not limited to stethoscopes or to medical device applications generally. Visual-acoustic devices in accordance with exemplary embodiments of the present invention can be used in a variety of sound analysis applications. These applications include, but are not limited to, non-destructive material analysis, seismology and other environmental and geological applications, oceanological applications, tactical applications and as motion or sound detectors for security systems.

The visual-acoustic device includes an acoustic detector 12 to produce sound waves associated with sounds generated by an object when the acoustic detector is placed in contact with the object, and a moiré pattern generator 14 in communication with the acoustic detector to receive the sound waves produced by the acoustic detector and to produce at least one moiré pattern corresponding to the sound waves. In one embodiment, the acoustic detector 12 includes a bell housing 24 and a diaphragm 22 covering an opening of the bell housing. As illustrated, the acoustic detector 12 is an acoustic stethoscope having a diaphragm 22 arranged to produce sound waves associated with sounds generated by internal organs of a living organism when the diaphragm 22 and bell housing 24 are placed in contact with an area of the living organism.

Visual-acoustic devices in accordance with the present invention are arranged to function with a typical acoustic stethoscope and do not appreciably affect the size or shape of a typical stethoscope. In addition, visual-acoustic devices in accordance with the present invention do not require electronic circuitry or sources of power to generate visual analogues of the sounds generated by an object of interest. Suitable objects of interest include, but are not limited to, the internal organs of humans and other animals, geological structures and marine animals.

In one embodiment, the diaphragm 22 and bell housing 24 form a conventional acoustical pickup head 12 that is well known and available in the medical device art. The diaphragm 22 converts acoustical pulses from the object being monitored, for example the acoustic pulses produced by the heart, pulse, blood flow or any other body sounds, into audible sound waves. The sound waves are delivered through an acoustic channel 18 and tubing 20 to ear pierces (not shown) that are inserted into the ears of the physician or other health care provider that is examining the patient. The bell housing 24, diaphragm 22, acoustic channel 18 and tubing 20 can be constructed from any suitable materials as are known and available in the art.

Visual-acoustic stethoscopes in accordance with the present invention provide visual as well as acoustic information on pressure changes generating measurable forces that are transmitted to a stethoscope-like pickup. Exemplary embodiments have an increased sensitivity over conventional acoustic stethoscopes. No additional complexity in operation is required for the user to obtain additional information to be used to make a diagnosis. The only correlation required concerns the relationships between moiré patterns created by various sounds and related pressure changes.

Figure 3:
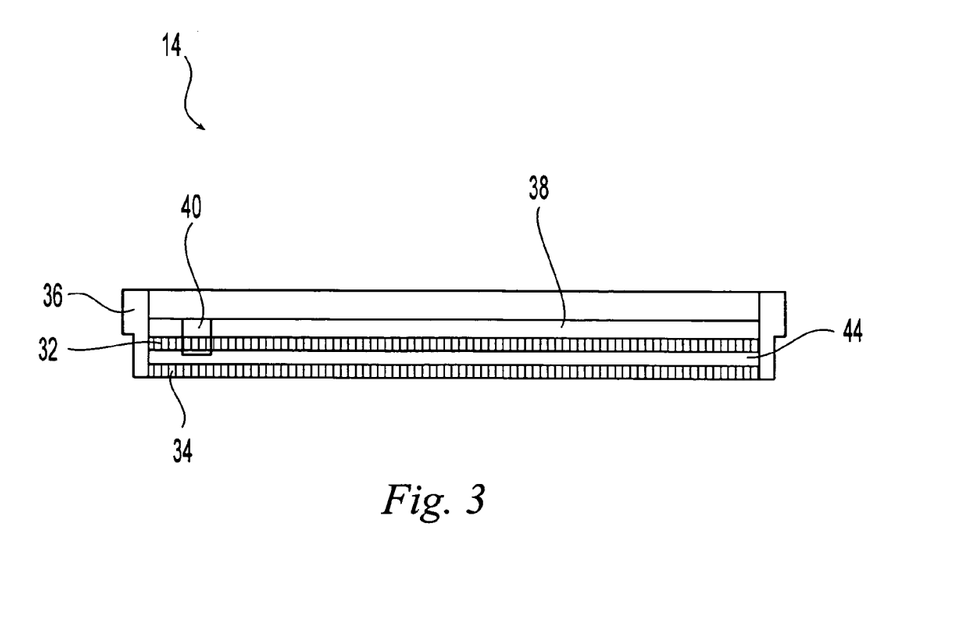
FIG. 3 is a view through line 3-3 of FIG. 1.

As shown in FIGS. 1-3, in one embodiment, the moiré pattern generator includes a rigid plate 32 that contains a first repetitive pattern and a flexible plate 34 spaced from the rigid plate 32. The flexible plate 34 contains a second repetitive pattern corresponding to the first repetitive pattern. Suitable materials for the rigid plate include plastics and other polymers and glass and are selected to be rigid enough to not flex or deform under the stresses associated with the sound waves or the use of the visual-acoustic device. Suitable materials for the flexible plate include plastics, polymers and glass and are selected to display the desired amount of flex when exposed to the sound waves generated by the acoustic detector. Suitable methods for applying patterns to the plates include, but are not limited to, machine etching of transparent, hard rigid plates into patterns suitable and sensitive enough for the desired use, coloring of the plates in particular if color differentiation is desired and placing transparencies containing patterns generated using computer graphics programs, i.e. spreadsheet and word processing programs, onto rigid transparent glass or plastic plates. In addition, the computer generated patterns are printed on transparent flexible membranes that are glued to supporting paper or backings. The paper is removed, and the flexible transparency is used as one of the plates.

Figure 7:
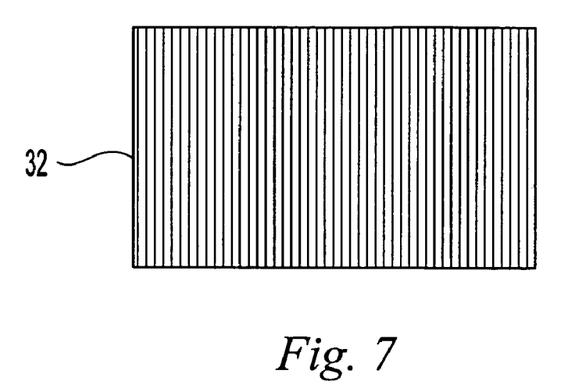
FIG. 7 is a view of an embodiment of a first repetitive pattern for use in the moiré pattern generator of the present invention.
Figure 8:
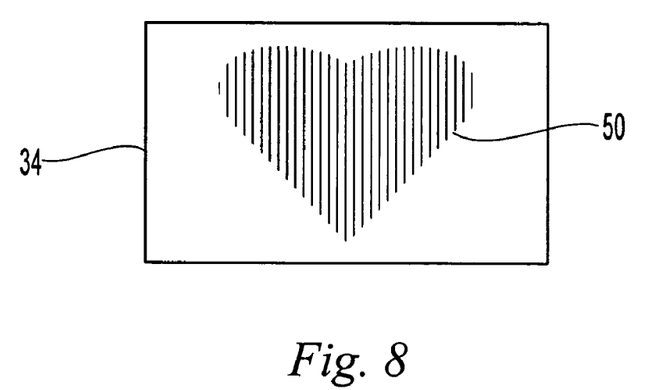
FIG. 8 is a view of an embodiment of a second repetitive pattern corresponding to the first repetitive pattern of FIG. 7.
Figure 9:
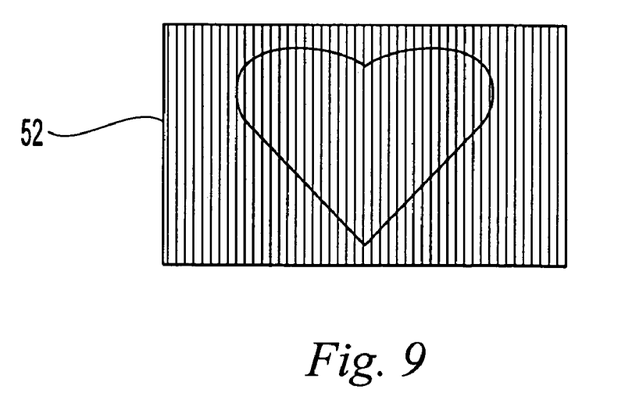
FIG. 9 is a view of the moiré pattern generated by the first and second repetitive patterns of FIGS. 7 and 8.

An embodiment of suitable patterns for use as the moiré patterns are illustrated in FIGS. 7-9. As is shown in FIG. 7, the rigid plate 32 includes a first pattern, which as illustrated is a series of equally spaced parallel lines. As is show in FIG. 8, the flexible plate 34 includes a second pattern 50 corresponding to the first pattern on the rigid plate. As illustrated, the second pattern 50 is shaped like a heart, but is constructed of a series of parallel lines corresponding to the parallel lines of the first pattern. The first and second patterns can also be printed in contrasting colors for increased visual differentiation. For example, the first pattern can be printed using blacks lines, and the second pattern can be printed using red lines. In general, the patterns do not have to occupy the entire surface of the plates. The sensitivity of the moiré pattern generator is dependent on grid line width and line spacing. Smaller the line widths and line spacings correspond to more sensitive generators. The pattern that is viewed by the user alternate between a view that is substantially the same as the pattern on the rigid plate 32 illustrated in FIG. 7 and a combination pattern 52 as illustrated in FIG. 9. As illustrated, the combination pattern 52 contains the heart shape pattern of the flexible plate. The visible pattern alternates between FIG. 7 and FIG. 9 in accordance with acoustic pressure changes. If the pressure changes exceed the sensitivity limits of the generator, the visible pattern will flicker between the two views in accordance with the pressure changes.

In general, the sound waves produce by the acoustic generator induce movement or flexing of the flexible plate such that the second repetitive pattern moves with respect to the first repetitive pattern to produce at least one moiré pattern. This moiré pattern corresponds to the sound wave generated by the acoustic generator and is correlated to the sound of the object that produced the sound wave. Therefore, by viewing the moiré pattern, qualities of the sound of the object being monitored are discernable visually. In medical applications, this permits a visual indication of the diagnosis of the internal organ being monitored. In one embodiment, at least one of the flexible plate, and the rigid plate is semi-transparent so that the respective overlay of the first and second fixed patterns can be viewed.

The moiré pattern generator can be tuned or modified in accordance with the sound waves that are anticipated from the object being monitored. In addition, the frequency selection of sounds being monitored is filtered by changing the diaphragm to enhance desired tones and to attenuate others. The moiré pattern generator is modified in accordance with the anticipated frequency of the modified sound or intensity of the sound waves. In one embodiment, the construction of either the rigid or flexible pattern plates is provided with varying curvatures, thicknesses, shapes or combinations thereof to create specific viewable patterns. For example, the flexible plate stiffness is selected to correspond to sound waves anticipated to be produced by the acoustic detector. In addition, the thickness and spacing of the lines in the fixed, repetitive patterns of either or both pattern plates may be constructed to create specific viewable patterns. In one embodiment, the rigid plate is rotatable with respect to the flexible plate to provide tuning of the moiré pattern in accordance with sound waves anticipated to be produced by the acoustic detector. For example, various rotational positions can correspond to experimentally known diagnostic settings. In another embodiment, the moiré pattern generator includes one or more additional plates, each additional plate comprising an additional corresponding pattern.

Since the flexible plate 34 is spaced from the rigid plate 32, an air space 44 having a pre-determined thickness is disposed between the flexible plate and the rigid plate. The air space permits the flexible plate to distort without being interfered with by the rigid plate. In one embodiment, the moiré pattern generator is provided with variable sensitivity by using an adjustable air space between the two repetitive patterns. For example, the flexible plate is moveable with respect to the rigid plate to affect a thickness of the air space between the rigid plate and the flexible plate. Movability can be accomplished by making the rigid plate, the flexible plate or both the rigid plate and the flexible plate removable. In one embodiment, the removal of the plates is facilitated by arranging the moiré pattern generator within a separate, self-contained housing 36 (FIG. 3) that can be attached to and separated from the acoustic generator housing 42 using any conventional attachment mechanisms. In addition, placing the moiré pattern generator in a self-contained housing 36 allows for creation of multiple moiré pattern generators that can be selected and attached to the acoustic generator housing 42 based upon the object to be monitored. Further, the moiré pattern generator housing 36 can be configured such that the moiré pattern generator can be retrofit onto existing acoustic generators such as existing stethoscopes. Suitable materials for the moiré pattern generator are the same as for the bell housing, and in one embodiment, the acoustic generator housing is formed integral with the bell housing. These materials include, but are not limited to metals such as aluminum and plastics.

In one embodiment, in order to protect the rigid plate and the fixed pattern contained thereon, a viewing window 38 is disposed over the rigid plate. Therefore, the moiré pattern is viewed through the viewing window 38. The viewing window can also be arranged as a convex or concave lens to assist in the viewing of the moiré pattern or to highlight one or more aspects of the moiré pattern. Since the flexible plate moves with respect to the rigid plate, changing the thickness of the air space between the two, a breathing hole 40 is provided in the rigid plate 32, and the viewing window 38. The breathing hole allows air, and any condensation, to escape from the air space during compression. In addition, air is allowed to freely enter the air space during expansions. Therefore, pressures or vacuums within the air space that could affect the response of the flexible plate to the sound waves are avoided. Suitable materials for the viewing window 38 include, but are not limited to transparent glass or plastic.

Figure 4:
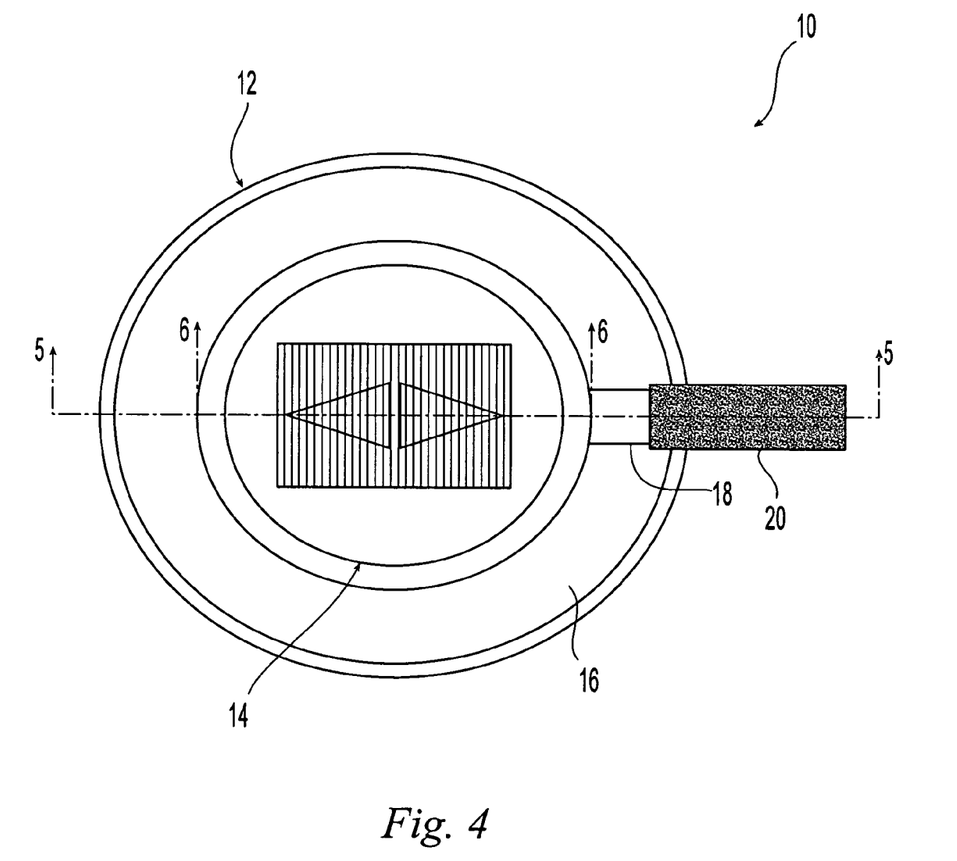
FIG. 4 is top view of another embodiment of a visual acoustic stethoscope in accordance with the present invention.
Figure 5:
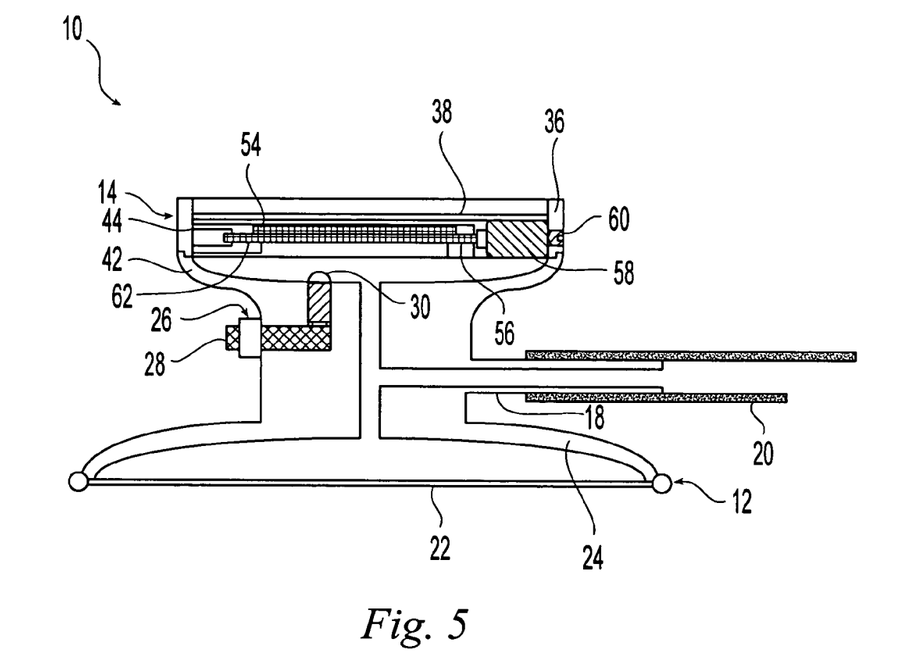
FIG. 5 is a view through line 5-5 of FIG. 4.
Figure 6:
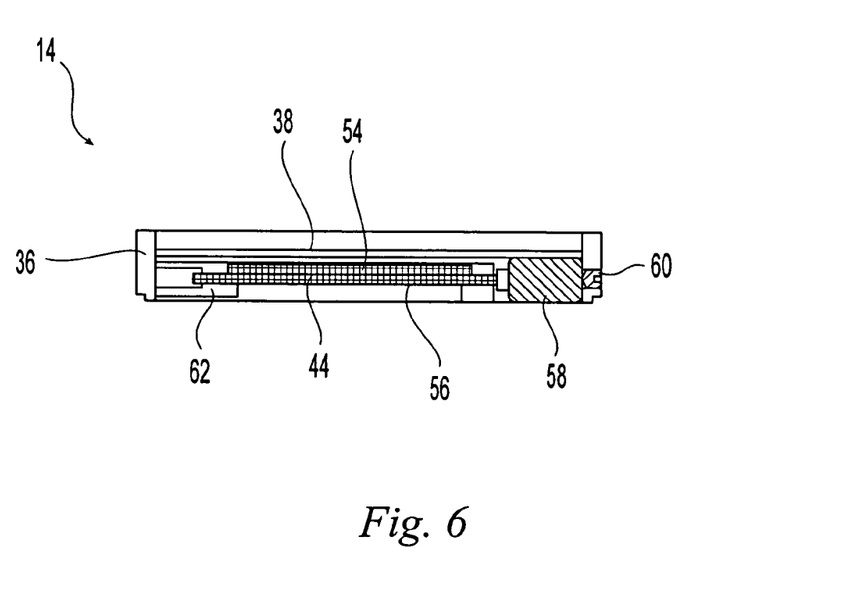
FIG. 6 is a view through line 6-6 of FIG. 4.

As shown in FIGS. 4-6, in another embodiment, the moiré pattern generator includes a first rigid, fixed semi-transparent plate 54 that contains the first repetitive pattern and a semi-transparent, rigid moveable plate 56 spaced from the fixed rigid plate 54. The moveable plate 56 is moveable with respect to the fixed plate and contains a second repetitive pattern corresponding to the first repetitive pattern. Suitable materials and methods for applying the patterns are the same as for the rigid plate 32 and flexible plate 34 embodiments. The moiré pattern generator also includes a sealed air sack 58 or other suitable flexible bladder in contact with the rigid moveable plate 56. The sealed air sack deforms in response to changes in pressure generated by the acoustic sounds waves. Also included in the moiré pattern generator is a sensitivity control 60 that controls the sensitivity or deformation of the sealed air sack 58 to the acoustic sound waves. In one embodiment, the sensitivity control 60 is a set screw that impinges on the sealed air sack and is used to increase or decrease the flexibility of the sealed air sack. The moiré pattern generator can also include internal supports 62 to provide for the support of the plates and the movement of the moveable plate with respect to the fixed plate. As shown in FIG. 6, the moiré pattern generator in accordance with this embodiment can be arranged in a separate, self-contained housing 36.

Figure 10:
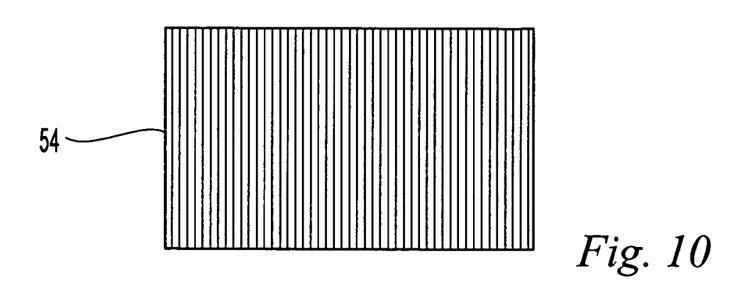
FIG. 10 is a view of another embodiment of a first repetitive pattern for use in the moiré pattern generator of the present invention.
Figure 11:
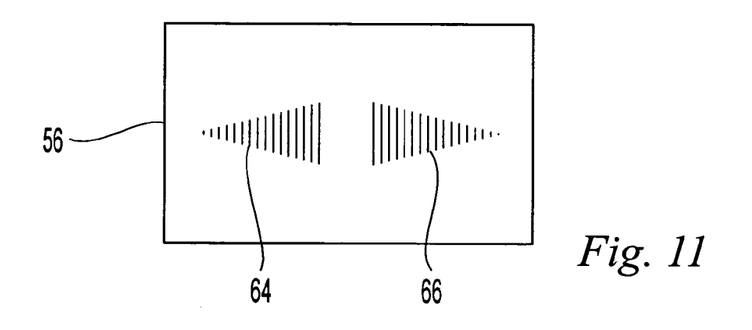
FIG. 11 is a view of another embodiment of a second repetitive pattern corresponding to the first repetitive pattern of FIG. 10.
Figure 12:
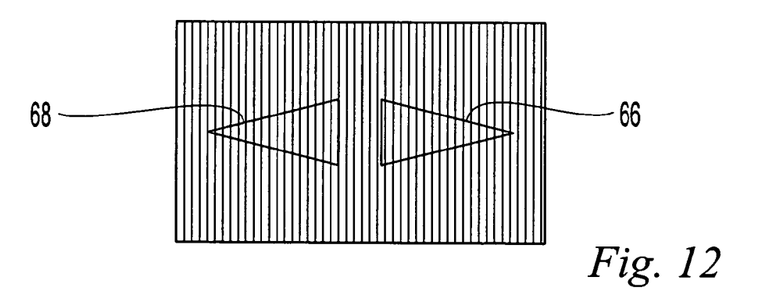
FIG. 12 is a view of a first moiré pattern generated by the first and second repetitive patterns of FIGS. 10 and 11.
Figure 13:
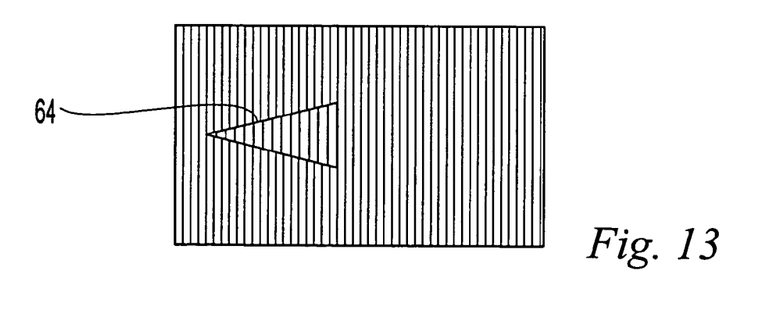
FIG. 13 is a view of a second moiré pattern generated by the first and second repetitive patterns of FIGS. 10 and 11.

An embodiment of suitable patterns for use as the moiré patterns are illustrated in FIGS. 10-13. As is shown in FIG. 10, the fixed rigid plate 54 includes a first repetitive pattern, which as illustrated is a series of equally spaced parallel lines. As is show in FIG. 11, the moveable rigid plate 56 includes a second repetitive pattern corresponding to the first pattern on the fixed rigid plate. As illustrated, the second pattern contains a first arrow or triangle 64 and a second arrow or triangle 66 pointing in a direction generally opposite the first triangle. Both of these triangles are constructed of a series of parallel lines corresponding to the parallel lines of the first pattern. The first and second patterns and the first and second triangles can also be printed in contrasting colors for increased visual differentiation. For example, the first triangle can be printed using green lines, and the second triangle can be printed using red lines. The pattern that is viewed by the user alternates between the view of FIG. 12 where the second triangle 66, including the triangle's color is completely visible and the outline of the first triangle 68 is visible and the view of FIG. 13 where the first triangle 64 including the triangle's color is completely visible. The visible pattern alternates between FIG. 12 and FIG. 13 in accordance with acoustic pressure changes. In general, the grid line positions for the first and second triangles, or left and right pointers, are such that when the first triangle is visible the second triangle is not visible and vice versa. Again, sensitivity of the generator is dependent on grid line width and line spacing. Smaller line widths and line spacings correspond to a more sensitive generator. Although illustrated as two embodiments, other pattern generators based on overlaying concentric circles, redial lines and spiral lines, among others, are also suitable for use with moiré pattern generators in accordance with the present invention.

In one alternative embodiment, a light generating assembly 26 is disposed within the visual-acoustic device 10 adjacent the moiré pattern generator to assist in viewing the moiré patterns produced by the generator. In one embodiment, the light generating assembly includes a switch 28, a light emitting member 30 such as a light emitting diode 30, and a power source (not shown). Suitable switches include push-button type switches. Any suitable type of light generating assembly that assists in viewing the generated moiré patterns without affecting the sensitivity and responsiveness of the visual-acoustic device can be used. If a visual assist is needed, the switch is pushed causing the light to illuminate and providing an illuminated background.

In one embodiment, the visual-acoustic stethoscope is provided as a stand alone visual stethoscope. As a stand alone visual device, the generated moiré patterns are used as inputs to a pattern interpretation program. The pattern interpretation program is used to analyze each more pattern and provide an associated diagnosis. In one embodiment, a moiré pattern interpretation system to analyze the produced moiré pattern and to associate each produced moiré pattern with one or more sounds is provided in communication with the moiré pattern generator.

In order to use the visual-acoustic device in accordance with the present invention to generate visual analogues of sound waves, the acoustic detector is placed in contact with an object that generates at least one sound. The acoustic detector produces sound waves that correspond to the sounds generated by the object. In additional to monitoring and listening to the sound waves, the sound waves are used to move corresponding first and second fixed patterns with respect to each other to generate a moiré pattern. In one embodiment, the sound waves are used to move a flexible plate containing the second fixed pattern with respect to a rigid plate containing the first fixed pattern.

In one embodiment, a hybrid visual acoustic stethoscope in accordance with the present invention containing a standard acoustic-bell or chest-bell having a diaphragm is placed by a medical practitioner on a body site overlying an internal region thereof such as the heart region, so as to pick up sounds emanating therefrom. The stethoscope is used in the normal manner by placing the diaphragm end against the body part to be monitored. The bell is coupled by a tubular line acting as an acoustic wave guide to a pair of acoustic earphones which are inserted in the ears of the physician using the stethoscope. The physician can therefore hear sounds emanating from the internal body region within the ambit of the bell.

When a sound compression wave enters the stethoscope, sound waves are transmitted to the standard ear pieces and also cause the flexible plate to distort. The distortion of the flexible plate causes a misalignment between the fixed, repetitive patterns, generating the moiré patterns in rhythm with the sounds being produced. The physician views the moiré pattern generated and compares this moiré pattern with known patterns to obtain additional diagnostic data.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

What is claimed is:

1. A visual-acoustic device comprising:
   an acoustic detector to produce sound waves associated with sounds generated by an object when the acoustic detector is placed in contact with the object; and
   a moiré pattern generator in communication with the acoustic detector to receive the sound waves produced by the acoustic detector and to produce at least one moiré pattern corresponding to the sound waves.

2. The device of claim 1, wherein the moiré pattern generator comprises:
   a rigid plate comprising a first repetitive pattern; and
   a flexible plate spaced from the rigid plate, the flexible plate comprising a second repetitive pattern corresponding to the first repetitive pattern;
   wherein the sound waves induce movement of the flexible plate such that the second repetitive pattern moves with respect to the first repetitive pattern to produce the at least one moiré pattern.

3. The device of claim 2, wherein at least one of the flexible plate and the rigid plate is semi-transparent.

4. The device of claim 2, wherein the rigid plate is rotatable with respect to the flexible plate to provide tuning of the moiré pattern in accordance with sound waves anticipated to be produced by the acoustic detector.

5. The device of claim 2, wherein the flexible plate comprises a stiffness corresponding to sounds waves anticipated to be produced by the acoustic detector.

6. The device of claim 2, wherein the flexible plate is moveable with respect to the rigid plate to affect a thickness of the air space between the rigid plate and the flexible plate.

7. The device of claim 2, wherein the moiré pattern generator further comprises one or more additional plates, each additional plate comprising an additional corresponding pattern.

8. The device of claim 1, further comprising a moiré pattern interpretation system to analyze the produced moiré pattern and to associate each produced moiré pattern with one or more sounds.

9. The device of claim 1, further comprising a light generating assembly disposed adjacent the moiré pattern generator to assist in viewing the moiré patterns produced by the generator.

10. The device of claim 1, wherein the acoustic detector comprises a bell housing and a diaphragm covering an opening of the bell housing.

11. The device of claim 1, wherein the acoustic detector comprise an acoustic stethoscope.

12. The device of claim 1, wherein the moiré pattern generator comprises:
   a rigid fixed plate comprising a first repetitive pattern;
   a rigid moveable plate spaced from the rigid fixed plate, the moveable plate comprising a second repetitive pattern corresponding to the first repetitive pattern;
   a sealed flexible air sack in contact with the moveable plate; and
   wherein the sound waves induce deformation of the flexible sealed air sack, inducing movement of the moveable rigid plate such that the second repetitive pattern moves with respect to the first repetitive pattern to produce the at least one moiré pattern.

13. The device of claim 12, further comprising a sensitivity control in contact with the flexible sealed air sack, the sensitivity control capable of controlling the deformation of the sealed air sack induced by the sound waves.

14. A visual-acoustic stethoscope comprising:
   an acoustic detector comprising a bell housing and a diaphragm covering an opening of the bell housing, the diaphragm arranged to produce sound waves associated with sounds generated by internal organs of a living organism when the diaphragm and bell housing are placed in contact with an area of the living organism; and
   a moiré pattern generator in communication with the bell housing of the acoustic detector to receive the sound waves produced by the diaphragm and to produce at least one moiré pattern corresponding to the sound waves.

15. The device of claim 14, wherein the moiré pattern generator comprises:
   a rigid plate comprising a first repetitive pattern; and
   a flexible plate spaced from the rigid plate, the flexible plate comprising a second repetitive pattern corresponding to the first repetitive pattern;
   wherein the sound waves induce movement of the flexible plate such that the second repetitive pattern moves with respect to the first repetitive pattern to produce the at least one moiré pattern.

16. The device of claim 14, further comprising a light generating assembly disposed adjacent the moiré pattern generator to assist in viewing the moiré patterns produced by the generator.

17. The device of claim 14, wherein the rigid plate is rotatable with respect to the flexible plate to provide tuning of the moiré pattern in accordance with sound waves anticipated to be produced by the acoustic detector.

18. The device of claim 14, wherein the flexible plate comprises a stiffness corresponding to the sounds waves anticipated to be produced by the acoustic detector.

19. The device of claim 14, wherein the flexible plate is moveable with respect to the rigid plate to affect a thickness of the air space between the rigid plate and the flexible plate.

20. A method for generating visual analogues of sound waves, the method comprising:
   placing an acoustic detector in contact with an object generating a sound;
   using the acoustic detector to produce sound waves corresponding to the generated sound; and
   using the sound waves to move corresponding first and second fixed patterns with respect to each other to generate a moiré pattern, wherein the sound waves move a flexible plate containing the second fixed pattern with respect to a rigid plate containing the first fixed pattern.

* * * * *